United States Patent
Bamdad et al.

(12) 
(10) Patent No.: US 6,830,050 B1
(45) Date of Patent: Dec. 14, 2004

(54) METHOD AND DEVICE FOR APPLYING PRESSURE TO THE WHOLE OF THE CHEST AREA OF POST CHEST SURGERY PATIENTS

(76) Inventors: Rafi Bamdad, 13250 Pierce Rd., Saratoga, CA (US) 95070; Amir Farsio, 18402 Llagas Creek Dr., Morgan Hill, CA (US) 95037; Hamid Mehdizadeh, 14928 Diduca Way, Los Gatos, CA (US) 95032

( * ) Notice: Subject to any disclaimer, the term of this patent is extended or adjusted under 35 U.S.C. 154(b) by 271 days.

(21) Appl. No.: 10/033,087

(22) Filed: Oct. 29, 2001

(51) Int. Cl.[7] ................................................ A61G 15/00
(52) U.S. Cl. ........................... 128/845; 128/846; 5/648
(58) Field of Search ................................ 128/845, 846, 128/874, 875; 602/5, 19; 5/648

(56) References Cited

U.S. PATENT DOCUMENTS

| | | | |
|---|---|---|---|
| 2,765,480 A | | 10/1956 | Mueller |
| 3,305,878 A | | 2/1967 | Hellbaum |
| 3,889,684 A | * | 6/1975 | Lebold ........................ 128/402 |
| 4,683,601 A | | 8/1987 | Lagin |
| 4,829,613 A | | 5/1989 | Yon |
| 5,154,691 A | | 10/1992 | Box et al. |
| 5,263,496 A | | 11/1993 | Cherniak |
| 5,297,304 A | | 3/1994 | O'Sullivan |
| 5,329,636 A | | 7/1994 | Siddle |
| 5,363,523 A | | 11/1994 | Blackburn |
| 5,566,682 A | | 10/1996 | Yavitz |
| 5,692,246 A | | 12/1997 | Benedick |
| 5,843,008 A | * | 12/1998 | Gerhard ......................... 602/5 |
| 6,263,876 B1 | | 7/2001 | Butts |

* cited by examiner

Primary Examiner—Michael A. Brown
(74) Attorney, Agent, or Firm—Ali Kamarei

(57) ABSTRACT

The invention described is a pressure device for applying pressure to the whole of the chest area of a patient and for reducing the movement and dehesion of the sternum and chest incision after open heart and chest surgeries. The pressure device has a casing substantially in the form of a pillow, the casing having opposing lateral sides, a back side for application against the chest of the patient, the back side having top corners, a frontal side substantially on the opposite side of the back side of the casing, the frontal side having a top attachment portion and a bottom attachment portion. A membrane layer attached to the top attachment portion and the bottom attachment portion of the frontal side of the casing, the outer wall of the frontal side and the inner wall of the membrane layer forming a sleeve for receiving the hands and forearms of a patient. A contiguous strap attached to the top corners of the back side for attachment of the casing around the neck of the patient for immediate proximity of the pressure device to the patient's chest incision area. A gripping handle is provided for engagement by the patient's hands.

8 Claims, 2 Drawing Sheets

METHOD AND DEVICE FOR APPLYING PRESSURE TO THE WHOLE OF THE CHEST AREA OF POST CHEST SURGERY PATIENTS

FIELD

The invention relates generally to treatment for patients after open-heart and chest surgeries. More specifically, this invention relates to applying pressure to the whole of the patient's chest area and to reduce dehesion of incisions post surgery.

BACKGROUND

Open heart and other chest surgeries have become pervasive in modern day medicine, accounting for numerous surgeries worldwide. Open-heart and other chest surgeries involve the cutting of the sternum bone along its medial line to separate the right rib cage from the left rib cage. This allows the heart and lung organs to be accessible to the surgeon and the equipment they use. After these types of surgeries are completed, the sternum bone has to be re-sewn together. For this, wires are used which help to hold the two sides of the cut sternum together. Holding the sternum together allows for the cut sternum once again to fuse together. Naturally, the cut sternum bones have to be aligned properly so that the process of fusing the bones can occur more rapidly and properly.

Although the cut sternum is sewn back together using wires, still movements in the chest area and chest muscles occur, which tend to cause dehesion or coming loose of the incision. Factors which contribute to movement of the chest area and ultimately dehesion of the incision are many. One of the side effects of open heart and other chest surgeries is that after surgery copious amounts of phlegm and other material such as blood will have to be expelled by coughing. In fact medical practitioners encourage patients to cough post surgery. Coughing causes a great deal of movement in the chest area causing movement in the incision area and movement where the cut sternum has been sewn together. Patients are also instructed not to use their hands and elbows to apply pressure to move when they are in bed. In order to get out of bed, patients must do so without using their hands. Additionally, patients are instructed not to perform any arm abduction movements. Movement in the chest area has to be suppressed as much as possible because of several reasons. First, movement of the pectoralis minor and pectoralis major muscles during arm movement, as well as movement caused by the contraction and expansion of the diagphram muscle, increases the chance for dehesion of the incisions. Movements in the incision area may cause dislocation of the sternum which increases the chance for infection of the chest area and the need for follow up surgeries. Second, improper fusion of the sternum or lack of fusion of the sternum would require re-cutting and/or re-attachment of the sternum. Finally, movement in the chest area is discouraged to reduce pain.

Other devices are currently being used to address some of the above-mentioned problems. The most popular of these devices is an ordinary pillow. A post surgery patient is given a pillow and instructed to apply pressure to the pillow during coughing. The drawback to this device is readily seen. First the patient must at all times hold the pillow over their chest. Coughing often occurs without notice and therefore, the patients must have the pillow available to them continuously. Additionally, when the patients are resting, their arms rest on their side. This position tends to stretch the pectoralis major and minor muscles and therefore acts to open the incisions in the sternum. Other devices used are seen in Lagin, U.S. Pat. No. 4,683,601, and Box et al. U.S. Pat. No. 5,154,691. Lagin discloses a medical pillow for use by patients who have undergone an open-heart surgery. The pillow eases the pain associated with coughing. Lagin also uses sleeves so that the patients' arms can "pull" the pillow against their chest. This device allows for patients to rest their arms over their chest and in times of unexpected coughing allows them to quickly force the pillow towards their chest. However, this device actually forces the pectoralis muscles to stay in a stretched or extended position and while it may reduce the pain during coughing, still the patients will be contracting their pectoralis muscles to force the pillow towards their chest which operates to open the incisions. The ideal device will aid the patients to exert pressure on their chest and at the same time not contract their pectoralis muscles. Box, et al. U.S. Pat. No. 5,154,691 provides a "cough pillow" that is in close proximity to the surgical area. For this, Box provides straps that go around the shoulder and back of the patient. This device provides no sleeve and simply requires the patient to exert pressure on the chest by pulling the pillow towards the chest area.

In view of the foregoing, there is a significant need for a device and method to reduce movement of the chest area after open-heart or other chest surgeries.

Furthermore, there is a need for a device and method for applying pressure to the whole of the chest area during coughing to prevent dehesion of incisions.

Additionally, there is a need for a device that is readily accessible to the patients without the patients having to move their arms for placement of the device over the chest area.

SUMMARY

The invention described is a pressure device for applying pressure to the whole of the chest area of a patient and for reducing the movement and dehesion of the sternum and chest incision after open heart and chest surgeries. The pressure device has a casing substantially in the form of a pillow or to receive a pillow. The casing has opposing lateral sides, a back side for application against the chest of the patient, the back side having top corners, a frontal side substantially on the opposite side of the back side of the casing, the frontal side having a top attachment portion and a bottom attachment portion. A membrane layer is attached to the top attachment portion and the bottom attachment portion of the frontal side of the casing, the outer wall of the frontal side and the inner wall of the membrane layer forming a sleeve for receiving the hands and forearms of a patient. A contiguous strap is attached to the top corners of the back side for attachment and support of the casing around the neck of the patient to provide for immediate proximity of the pressure device to the patient's chest incision area. A gripping handle is also provided, for the patient to grab with his/her hands.

Optionally, the gripping handle has first and second handle portions, wherein the first and second handle portions are positioned on the opposing lateral sides of the casing.

The method of the invention discloses reducing the movement and dehesion of the sternum and chest incision of a patient after open heart and chest surgeries. The method has the following steps. The pressure device is placed on the chest area of the patient, the pressure device having a casing substantially in the form to receive a pillow as described herein, the casing having opposing lateral sides, each lateral side having a gripping handle. Supporting the casing around the neck of the patient provides for positioning the pressure device in the immediate proximity of the patient's chest incision area. The patient then hugs the pressure device by extending the forearms through the sleeve formed by the membrane, thereby crossing the forearms over the pressure device, gripping the gripping handles on the opposing lateral sides, and then exerting pressure on the pressure device for reducing the movement and dehesion of the sternum.

Another method of the invention comprises expediting fusion of the cut sternum bone after open heart and chest surgeries. The steps for accomplishing fusion of the sternum bone comprises placing a pressure device on the chest area of the patient, the pressure device having a casing substantially in the form of, or to contain, a pillow, the casing having opposing lateral sides, each lateral side having a gripping handle. The method further includes supporting the casing around the neck of the patient for positioning the pressure device in the immediate proximity of the patient's chest incision area. Additionally, the method includes hugging the pressure device by crossing the forearms over the pressure device and gripping the gripping handles on the opposing lateral sides, thereby exerting pressure on the pressure device for reducing the movement and dehesion of the sternum. Alternatively, the method of the invention includes inserting the hands and the forearms into a sleeve positioned on the front surface of the casing.

DETAILED DESCRIPTION

This invention provides a device and method for applying pressure to the whole of the chest area of a patient and for reducing the movement and dehesion of the sternum and chest incision after open-heart or other chest surgeries.

Figure 1:
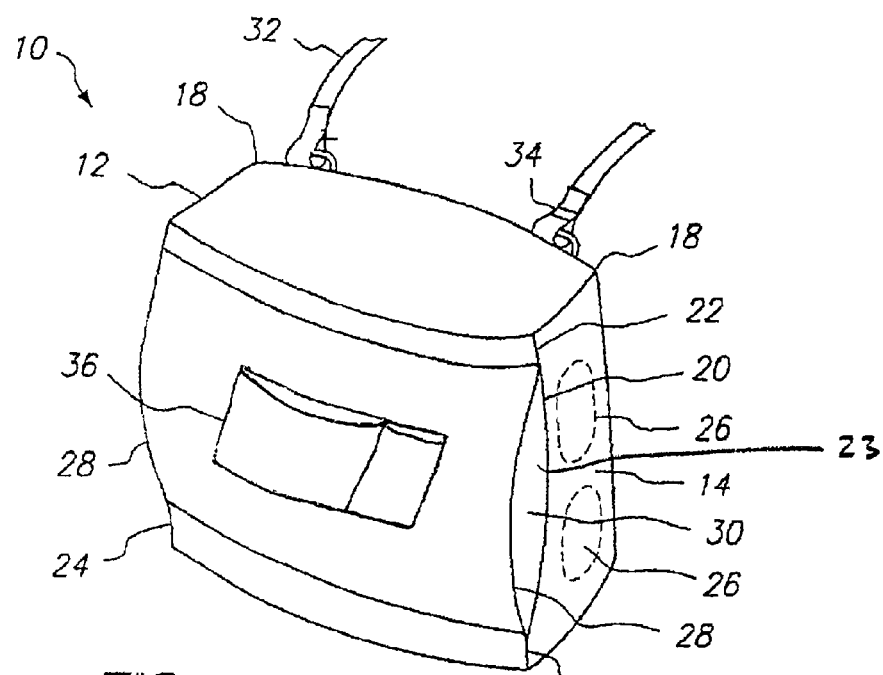
FIG. 1 shows a front perspective view of a first embodiment of the device of the invention showing the pressure device having gripping handles.

As shown in FIG. 1, a pressure device 10, comprises a casing 12, a contiguous strap 32, and gripping handles 26. The casing 12 further comprises opposing lateral sides 14, a casing back side 16, and casing frontal side 20. The plane of the casing back side 16 is substantially parallel to, receives, and is applied against the chest area of a patient. In one embodiment, the plane of the casing frontal side is substantially parallel to the plane of the casing back side. The casing 12 alternatively has a zipper, clasp, or button mechanism (not shown) such that a pillow or some filling material (not shown) is removably placed inside the casing 12. This allows for washing the casing after removing the pillow. The casing preferably has the following dimensions, its length (top to bottom) is approximately 14 inches, its width lateral side to lateral side) 10 inches and its thickness 4.5 inches. The casing is optionally manufactured using soft material such as foam or cotton, or optionally manufactured from semi-rigid material such as vinyl or plastic. Depending on the choice of the patient, various sizes, densities, types (such as air pillows), and shapes of pillows or filling material are optionally used within the casing.

The casing back side 16 has top corners 18, which are more proximate to the chin area of a patient. Connected to the top corners 18 is preferably a contiguous strap 32 which strap is placed around the neck of the patient. The benefit of placing a strap around the neck of a patient instead of around the shoulders and back is readily seen. Keeping the casing 12 in close proximity to the patient in an emergency situation, without forcing the patient to "put on" or "take off" the strap, is desirable as no appreciable movement of the patient's arms is required, and thereby no movement of the chest area occurs when a strap is placed over the neck of the patient by a nurse or medical assistant. In an embodiment a cam buckle (not shown) is use for lengthening or reducing the length of the strap 32 around the neck of the patient thereby providing the means for adjustable positioning of the casing over the chest area of the patient.

Figures 3, 4:
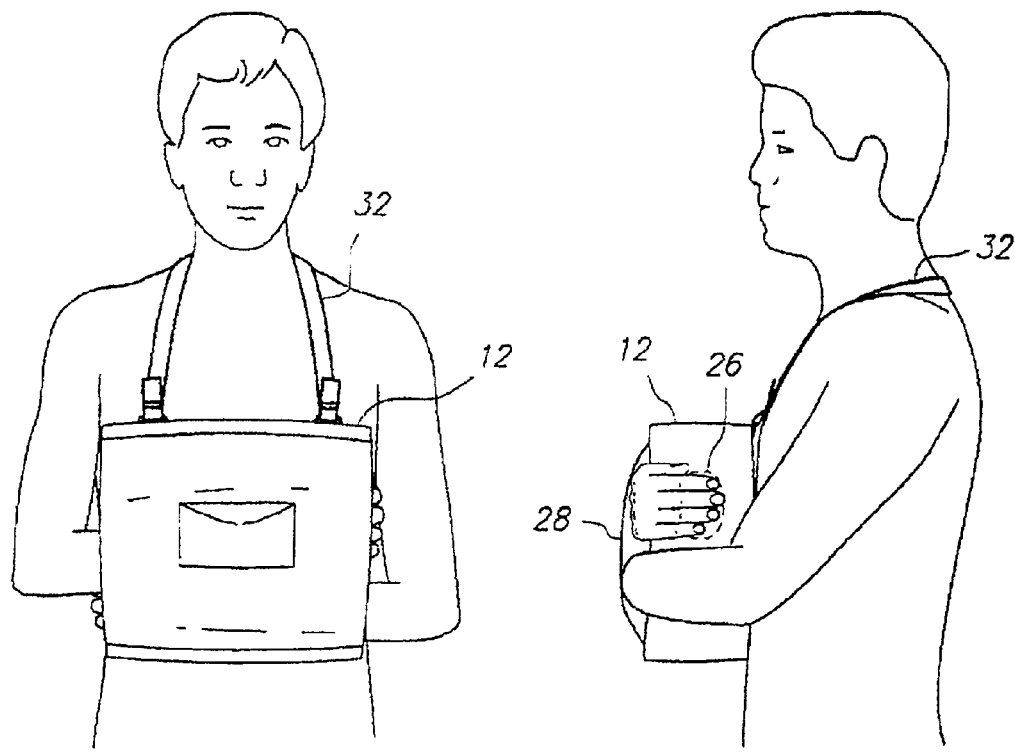
FIGS. 3 and 4 show a front and side view of a patient using the pressure device of the invention by gripping the gripping handles.

A membrane layer 28 is fixed to the top attachment portion 22 and bottom attachment portion 24 of the frontal side 20. The top attachment portion 22 and bottom attachment portion 24 are spaced a distance away from each other, thus, the outer wall 23 of the frontal side 20 and the inner wall 29 of the membrane 28 form a sleeve 30. The sleeve 30 is for receiving the hands and forearms of the patient. Sleeve 30 is preferably sufficiently large so that both hands and forearms of the patient is contained within the sleeve 30. The benefit of receiving the hands and forearms, as shown in FIGS. 3 and 4 can be seen. Ordinarily, especially when in a supine position, the arms tend to dangle or hang from the sides of the patient, which stretch the pectoralis major and pectoralis minor muscles, thereby causing pain to the patient and more importantly, operates as a force towards dehesion of the incision in the sternum. While in the position shown in FIGS. 3 and 4, the arms of the patient are aligned toward the center of the body of the patient in a crossed position, with little or no pressure exerted on the pectoralis major and pectoralis minor muscles. Additionally, the sleeve supports the forearms from dropping down toward the ground when in a supine position. It is understood that the patient can position the pressure device over the chest area when in bed as well. Furthermore, since the patient is already in this position, when an unexpected cough approaches, the patient quickly grabs the gripping handles to exert pressure on the whole of the chest area. As can be seen, the arms of the patient are in a "crossed" position posture. As used herein this means that the right hand is extended towards the left side of the body of the patient and the left hand is extended towards the right hand side of the body of the patient. Therefore, the hands of the patient can be quickly used to grab the opposing gripping handles located on the lateral sides of the casing which allows the patient to exert pressure on the whole of his/her chest area without contracting their pectoralis major and pectoralis minor muscles. Additionally, this "crossed" posture expedites the fusion of the sternum as the cut sternum bones are continuously kept in close contact with each other.

In an alternative embodiment, the pressure device of the invention has an accessory pocket 36 for containing various equipment needed by the patient.

Gripping Handles

Various alternative embodiments and structures operate to function as gripping handles 26. In a first embodiment, gripping handles are depressions within the opposing lateral sides 14 of the casing. Alternatively, gripping handles are protrusions on the lateral sides of the casing 12. Preferably, the area of the depression or protrusion gripping handles are sufficiently large to receive the fingers of the patient. In an alternative embodiment, the gripping handle is the lateral side of the casing itself that is of sufficient thickness. In a preferred embodiment, the casing lateral side is at least 2 inches thick. In another embodiment, the casing lateral side is at least 3 inches thick. In a preferred embodiment, the gripping handles are 4.5 inches thick. Preferably, in all embodiments, the gripping handle 26 is contoured or has serrations that are applied against and engage the finger tips of the patient.

Cooling and Heating Apparatus

Figure 2:
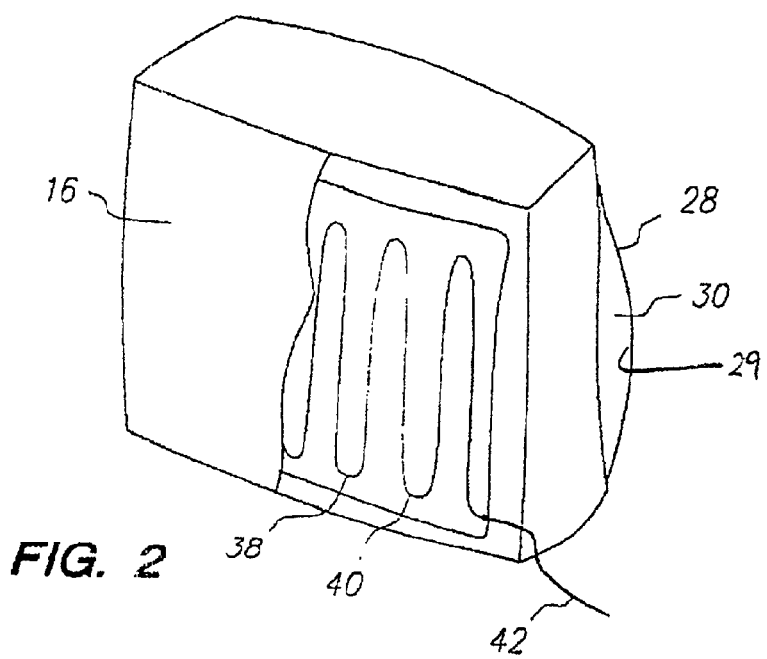
FIG. 2 shows a back perspective view of an alternative embodiment of the invention having a heating apparatus.

As seen in FIG. 2, in an alternative embodiment, casing 12 has heating apparatus 38 further comprising heating element 40 and access 42 to an electrical source, (not shown). The heating apparatus is preferably positioned inside the casing 12, in close proximity to the casing back side 16 so that heat is easily transferred to the chest area of the patient. Alternatively, a cooling device is placed in the position of the heating element 40 inside the casing 12, in close proximity to casing back side 16 so that the patient's chest area is cooled.

Method of Exerting Pressur on the Whole of the Chest Area

The method of the invention for reducing the movement and dehesion of the sternum and chest incision of a patient after open heart and chest surgeries comprises placing a pressure device on the chest area of the patient, the pressure device having a casing substantially in the form of a pillow or to enclose a pillow or the like, opposing lateral sides, each lateral side having a gripping handle. The casing is supported around the neck of the patient, therefore, the pressure device is positioned in the immediate proximity of the patient's chest incision area at all times. The patient then crosses his/her forearms over the pressure device and hugs the pressure device, thereafter gripping the gripping handles on the opposing lateral sides. By exerting pressure on the casing using the forearms and gripping the handles, the pressure device is used for reducing the movement and dehesion of the sternum. Using this method, the patient applies pressure across the whole of the chest surface area from the lateral sides over the frontal side of the pillow. The pressure applied across the chest surface area from the lateral side to the frontal side of the pillow is preferably accomplished by pressing down the elbows of the patient towards the chest area using the latismus dorsi muscles.

The gripping handles are optionally gripped either by the patient first inserting their hands and forearms through the sleeve 30, or over the sleeve 30.

In an alternative embodiment, the method of the invention further comprises adjustably positioning the pressure device over the patient's chest area. In yet another embodiment, the chest area of the patient is heated. Optionally, in another embodiment, the chest area of the patient is cooled.

From the foregoing, it will be appreciated how the objectives and features of the above-described invention are met.

First, the invention provides a device and method to reduce movement of the chest area after open-heart or other chest surgeries.

Furthermore, a device and method is shown for applying pressure to the whole of the chest area during coughing to prevent dehesion of incisions.

Additionally, a device is disclosed that is readily accessible to the patient without the patient having to move his/her arms for placement of the device over the chest area.

Furthermore, the invention provides a method for maintaining the cut sternum bones after a chest surgery in close proximity to each other and reduced movement to expedite fusion of the cut sternum bones together.

Although the invention has been described with respect to a particular pressure device and technique for applying pressure to the whole of the chest area of a patient, it will be appreciated that various modifications of the device and method are possible without departing from the invention, which is defined by the claims set forth below.

What is claimed is:

1. A method of reducing the movement and dehesion of the sternum and chest incision of a patient after open heart and chest surgeries comprising:

a. placing a pressure device on the chest area of the patient, the pressure device having a casing substantially in the form of a pillow, the casing having opposing lateral sides, each lateral side having a gripping handle, b. supporting the casing around the neck of the patient, for positioning the pressure device in the immediate proximity of the patient's chest incision area, c. hugging the pressure device by crossing the forearms over the pressure device and gripping the gripping handles on the opposing lateral sides, and d. exerting pressure on the pressure device for reducing the movement and dehesion of the sternum.

2. The method of claim 1 further comprising the patient applying pressure across the chest surface area from the lateral side to the frontal side of the casing.

3. The method of claim 2 wherein pressure is applied across the chest surface area from the lateral side to the frontal side of the casing by pressing down the elbows of the patient towards the chest area using the latismus dorsi muscles.

4. The method of claim 1 further comprising adjustable positioning of the pressure device over the patient's chest area.

5. The method of claim 1 wherein the chest area of the patient is heated.

6. The method of claim 1 wherein the chest area of the patient is cooled.

7. A method of expediting fusion of the cut sternum bone after open heart and chest surgeries comprising:

a. placing a pressure device on the chest area of the patient, the pressure device having a casing substantially in the form of a pillow, the casing having opposing lateral sides, each lateral side having a gripping handle, b. supporting the casing around the neck of the patient for positioning the pressure device in the immediate proximity of the patient's chest incision area, c. hugging the pressure device by crossing the forearms over the pressure device and gripping the gripping handles on the opposing lateral sides, and d. exerting pressure on the pressure device for reducing the movement and dehesion of the sternum.

8. The method of claim 7 herein the hands and forearms are inserted through a sleeve.

* * * * *